United States Patent [19]

Willging

[11] Patent Number: 4,550,183
[45] Date of Patent: Oct. 29, 1985

[54] PURIFICATION OF TOCOPHEROLS

[75] Inventor: Stephen M. Willging, Minneapolis, Minn.

[73] Assignee: Henkel Corporation, Minneapolis, Minn.

[21] Appl. No.: 636,884

[22] Filed: Aug. 2, 1984

[51] Int. Cl.$^4$ .......................................... C07D 311/72
[52] U.S. Cl. .................................................. 549/413
[58] Field of Search ........................................ 549/413

[56] References Cited

U.S. PATENT DOCUMENTS 2,263,550 11/1941 Andrews ............................ 549/413
3,122,565 2/1964 Kijima et al. ...................... 549/413

Primary Examiner—Nicky Chan
Attorney, Agent, or Firm—Ernest G. Szoke; Patrick J. Span; Robin M. Davis

[57] ABSTRACT

This invention relates to the purification and concentration of tocopherol compounds from an organic feed material containing these compounds. A sufficient amount of caustic methanol is used to contact a tocopherol-containing organic material whereby two phases are formed; one of which is tocopherol-enriched caustic methanol. The phases are separated and the caustic is neutralized. The tocopherol is then recovered from the tocopherol-enriched methanol. One way of recovery is by adding a sufficient amount of water, causing the tocopherol to form a separate phase, which can then be removed in this more purified, concentrated form. Alternatively, the tocopherol can be isolated by removal of the methanol by distillation after acidic neutralization, and then washing the tocopherol with water to remove the salt resulting from neutralization.

14 Claims, No Drawings

PURIFICATION OF TOCOPHEROLS

BACKGROUND OF THE INVENTION

Tocopherol compounds, also designated as Vitamin E, are the active components of certain vegetable oils. Vitamin E activity refers to the physiological activity of this group of nutrient materials. Materials having Vitamin E activity all belong to a distinct series of compounds which are all derivatives of chroman-6-ol. These compounds are all tocol derivatives having an isoprenoid $C_{16}$ side-chain, including those compounds having an unsaturated $C_{16}$ side chain. The term "tocol" is used to mean 2-methyl-2-(4',8',12'-trimethyltridecyl) chroman-6-ol. Alpha-, beta-, gamma- and delta-tocopherols are of primary importance for Vitamin E activity, and are commercially isolated from various natural sources. Also important are the enols such as tocodienols and tocotrienols which are tocopherol compounds having an unsaturated side chain. Within this description the terms "tocopherols" and "tocopherol compounds" are understood to include such unsaturated toco-enol compounds.

Tocopherols, found widely distributed in organic substances, occur in highest concentrations in cereal grain oils, principally in wheat and corn oils, and also in barley and rye. They are also found in vegetable oils such as safflower, soybean, peanut, cottonseed, linseed, sunflower, rapeseed, palm, and in other vegetable sources.

In general, tocopherols are widely used for their antioxidant and Vitamin E activity. They are of great value in foods, feeds and medicines for these reasons. Frequently, mixtures of tocopherols are isolated, purified, and methylated to upgrade Vitamin E activity.

Those tocopherol compounds having an unsaturated $C_{16}$ side-chain such as tocotrienol can be hydrogenated and then the beta, gamma, and delta isomers can be upgraded to alpha-tocopherol vitamin E activity.

Natural vegetable oils contain small amounts of tocopherols. Such oils as wheat germ oil, soybean oil, and cottonseed oil are considered to be the best sources of Vitamin E. It is desirable for commercial purposes to separate and concentrate tocopherol-containing materials and to devise methods for separating impurities from tocopherols so that they may be employed for their anti-oxidant and Vitamin E activity. A variety of methods have been developed which accomplish this. One such method is reported in U.S. Pat. No. 3,122,565 which involves mixing tocopherol-containing material with a polar organic solvent and contacting this mixture with a strongly basic anionic exchange resin whereby tocopherols are adsorbed on the resin. The tocopherols can then be eluted by passing an acidic eluding solution through the resin. Difficulties such as fouling frequently develop with resin systems. Resins furthermore have a low capacity, are shortlived and expensive. It would therefore be advantageous to develop methods for isolating and purifying tocopherol compounds which may be done continuously and without the use of resins. A method is described herein whereby tocopherols may be effectively extracted and purified in a liquid extraction system. When, in accordance with the instant invention, caustic methanol is used to extract and purify tocopherols, impurities such as squalene, dehydrated sterols, and waxes are separated and removed from the tocopherol.

BRIEF DESCRIPTION OF THE INVENTION

Tocopherol compounds can be purified and concentrated by contacting a tocotrienol or tocopherol-containing organic material such as vegetable oil with a sufficient amount of caustic methanol to form two phases. These phases are: (1) a tocopherol-enriched caustic methanol phase containing the tocopherol compounds; and (2) a second phase made up of the organic material which previously contained the tocopherol compounds now found in the caustic methanol phase. This organic material, which includes the impurities such as squalene, waxes, and sterols, is substantially immiscible with the caustic methanol phase and can be separated from the tocotrienol or tocopherol-enriched caustic methanol phase. These two phases are then separated and the caustic methanol phase is neutralized with an acid or salt thereof having a $pK_a$ less than that of the tocopherols acceptably those having a $pK_a$ less than 10 preferably those having a $pK_a$ less than 8. After neutralization the tocopherol is isolated or recovered from the methanol and the salt resulting from neutralization. This can be accomplished in several different ways, and different steps or mechanisms can be used in a variety of sequences resulting in the recovery of the tocopherol from the neutralized solution which has been purified by separation from its organic impurities.

While the main thrust of this invention is to separate and concentrate the alpha-, beta-, gamma-, and delta-tocopherols from other organic impurities, the unsaturated tocopherols, such as tocotrienol, which is a compound which differing from tocopherol only in that the $C_{16}$ side chain is unsaturated, is likewise valuable for Vitamin E activity and can also be separated. Since there are chemical processes available which upgrade tocotrienol and the non-alpha isomers to the Vitamin E activity of alpha-tocopherol, it can be desirable to use the instant invention to extract tocotrienols. It should also be noted that when toco-enols are present with tocopherol homologues, the instant invention will extract, purify and isolate these compounds along with the other tocopherols. The toco-enols having beta, gamma, and delta configurations can be used advantageously as, for example, by subjecting such a product to hydrogenation and methylation to yield alpha-tocopherol thereby increasing Vitamin E activity. It should therefore be understood that, the unsaturated tocopherols such as tocotrienol, tocodienols, and other toco-enols are included if found in the feed material. The unsaturated toco-enols are thus dealt with as the tocopherol homologues are and, as previously indicated, the term "tocopherol" as used generally herein will include the unsaturated tocopherol homologues such as the toco-, mono-, di- and tri-enols.

DETAILED DESCRIPTION OF THE INVENTION

The instant invention can be used to separate alpha-, beta-, gamma- and delta-tocopherol from their organic sources leaving the tocopherols in a more purified form. Even materials that are as low as 2% by weight (wt.) tocopherol homologues can be used as starting material for this process. Natural organic sources such as vegetable oils and plant materials can be used as the tocopherol-containing organic material feed for the instant invention. Representative, but non-exhaustive examples of such suitable substances are: safflower, soybean, peanut, cottonseed, linseed, sunflower, rapeseed, and palm oils. The starting material can also be taken from other plant sources such as palm leaves, lettuce, alfalfa, rubber latex and a variety of other plant materials.

Methanol is used as the extracting solvent for the tocopherols. Other alcohols such as ethanol, however, could be used in similar extractions if they are capable of solvating the caustic without degradation. Other alcohols, however, preferably are used with any aliphatic hydrocarbon solvent which can form a separate phase holding the organic impurities. These alcohols may require a different hydrocarbon solvent than methanol uses. Ethanol, for example, could be used but to extract the tocopherol the use of an aliphatic hydrocarbon solvent is preferred, and this solvent preferably is at least a $C_8$, and composed of a single isomer.

The present invention can also be used to purify tocopherol homologues from a starting material that is as high as 90% by wt. pure in these compounds. Frequently vegetable oils are used to produce a concentrate that is up to 60% mixed tocopherol. The instant invention can be used to further purify and isolate the tocopherols in such materials. Advantageously, residual sterols, squalene, and hydrocarbon impurities present along with the tocopherol homologues in such mixtures can be separated and removed by this process. In fact, even when the starting material is as high as 90% pure tocopherol homologues the instant invention can be used to remove impurities, and further purify the tocopherols. There is thus, no critical amount of tocopherol necessary in the starting material to use the process of the instant invention.

It should be noted that carboxylic acids have a tendency to enter the caustic methanol phase. The starting materials should therefore be preferably be low in carboxylic acids when a tocopherol product is desired which is free of such acids. Most preferably the starting material should be sufficiently low in carboxylic acids relative to the amount of desired compounds present.

When water is present with the caustic methanol, the phases formed are a tocopherol-enriched aqueous caustic methanol phase and a second phase containing organic impurities. If an aliphatic hydrocarbon solvent is used also, only a small amount of this solvent will solvate with the tocopherol and the caustic methanol- (aqueous or non-aqueous), but in doing so will aid in the extraction of tocopherol. The aliphatic hydrocarbon solvent should be used in a sufficient amount to maintain a two phase system. Most of the aliphatic hydrocarbon solvent will solvate the organic impurities in the second phase and can then be separated and either discarded or subjected to a second wash with another portion of caustic methanol to remove residual tocopherol.

The purified tocopherol solvated in the neutralized methanol phase can be recovered from the methanol phase by distillation. Such a distillation can remove both the methanol and any aliphatic hydrocarbon solvent, or the aliphatic solvent can be left with the tocopherol as a solvent for further processing. Any water present can also be distilled, or can be separated as a separate phase after the methanol is distilled. Conveniently, the salt formed can be removed with the water if it is water soluble, or filtered if it is not. Typically, when distillation is used to isolate the tocopherol from the more volatile materials, the salt can be either filtered as a solid precipitate, or is removed by washing the tocopherol residue with water. Preferably the tocopherol residue is washed at least twice with water, whether or not such a distillate includes an aliphatic hydrocarbon solvent along with the tocopherol. Distillation can be used in the recovery of the tocopherol instead of or in addition to both the phase formation, separation method of recovery or the aliphatic hydrocarbon extraction method of recovery. In such a case, a partial distillation of the volatiles away from the desired tocopherol can be used until phase formation occurs or until extraction with an aliphatic hydrocarbon solvent is appropriate. In either case the tocopherol-enriched material is separated and one or more water washes can be used to insure complete salt removal.

Formation of a separate tocopherol phase can also be used to recover the tocopherol. Neutralization, in addition to the presence of a sufficient quantity of water, is necessary to cause tocopherol to form such a phase, which can then be separated. When an aliphatic hydrocarbon solvent is used in the initial extraction of the tocopherol from its organic impurities, a portion of the aliphatic hydrocarbon will be present with the tocopherol and will separate with it in phase formation. In this case the aliphatic hydrocarbon can be left with the tocopherol and further treated by such processes as methylation or it can be removed by distillation, leaving the tocopherol.

When using the phase formation method to recover the tocopherol from the methanol solution, a sufficient amount of water is needed in addition to neutralization. This water can be added during neutralization by using an aqueous acid or by the separate addition of water. If this amount of water was not added in neutralization, then after neutralization a sufficient amount of water can be added to the tocopherol-enriched, neutralized methanol to cause this phase formation. A sufficient amount of water can also be added before neutralization to the separated tocopherol-enriched caustic methanol, in which case tocopherol phase separation will take place during neutralization. The phases resulting from the presence of water are: (a) an aqueous methanol phase having the salt formed from the caustic and the neutralizing acid; and (b) a tocopherol phase which can also have a small amount of an aliphatic hydrocarbon solvent which can permissably be used with the caustic methanol in the first extraction step. When separating the tocopherol by phase separation it is preferred to add the water during neutralization.

If, however, a sufficient amount of water was not previously added to the tocopherol-enriched caustic methanol before neutralization, then tocopherol separation will not occur, or will not be completed during neutralization unless water is added. In such a case, water can be added during or after neutralization until the tocopherol phase separation is completed, after which the separated tocopherol phase can be removed.

Another method which can be used is to select an acid and base which, in the methanol, forms a totally or partially insoluble salt resulting in a precipitate. Filtration is used to remove the precipitate, and the tocopherol can be recovered by either distillation, extraction, or phase formation and separation. The methanol collected after distillation or filtration of the solid salt precipitate can be reused. Representative but non-exhaustive examples of acids which can be used to form such salts which are totally or partially insoluble in the methanol are the mineral acids such as sulfuric, phosphoric or hydrochloric acids.

As previously indicated, a preferred embodiment of this invention is to use a non-polar aliphatic hydrocarbon solvent along with the caustic methanol to improve the first phase separation, tocopherol extraction and impurities separation. The order of addition of the aliphatic hydrocarbon solvent is not critical. Moreover, it can be used to contact the tocopherol-enriched caustic methanol, or the two phase system of the organic feed tocopherol source and the tocopherol-enriched caustic methanol. The aliphatic hydrocarbon must be substantially immiscible in the caustic methanol so that most of this solvent will be removed with the impurities, although a small portion of it will solvate with the tocopherol in the caustic methanol.

When combining the aliphatic hydrocarbon solvent, the tocopherol-containing impure organic feed material, and the caustic methanol, the manner and order of addition of these materials is not critical, except that it would be preferred to mix the base and the methanol before addition to the tocopherol-containing material.

A small portion of the hydrocarbon solvent will be solvated with the tocopherol in the caustic methanol, and will separate with the tocopherol if a second phase formation is used to isolate the tocopherol, although it can also be removed by distillation with the methanol. When the tocopherol, along with any aliphatic hydrocarbon solvent is separated from the methanol by phase separation, the hydrocarbon solvent can then also be removed by distillation, although it could be convenient to leave the tocopherol in the solvent if further processing, such as methylation of the beta, gamma, and delta tocopherols, is intended.

Another preferred embodiment, permits the addition of water to the caustic methanol in the first step of the process. The manner or order of addition of the water is not critical. It can, for example, be pre-mixed with the methanol or added directly to the feed material. When water is present in excess of from about 5% by wt. of the methanol, tocopherol separation can begin during neutralization if a sufficient amount of tocopherol is present, although more water must be added to complete phase separation.

When water is added to the caustic methanol, in extracting the tocopherol from the organic feed material, an aliphatic hydrocarbon should be added since a limited amount of this solvent will solvate with the tocopherol in the methanol. This is an aid to obtain the optimum tocopherol extraction when water is present.

Caustic is needed to solvate the tocopherol with the methanol. Suitably, any base which is soluble in the methanol can be used. Representative, but non-exhaustive examples of suitable bases are sodium hydroxide, potassium hydroxide, lithium hydroxide, and barium hydroxide or the corresponding methoxides. Acceptably, the amount of caustic used is from about 0.1% to about 10% by wt. of the methanol; preferably the caustic should be present in an amount of from about 0.5 to about 10% by wt. of the methanol.

When water is present, the total amount of caustic and water combined preferably is not greater than about 10% by weight of the methanol. Thus, the amount of water present in the caustic methanol for the first extraction should not be greater than 9.9% by weight methanol, since caustic should be present in a minimum amount of 0.1% by weight of methanol. While caustic can be present up to about 10% by weight of methanol, if water is present, the maximum amount of caustic is preferably limited to about 9.9% by weight of methanol, allowing for at least a small amount of water (about 0.1% by weight of methanol). When water is present in the caustic methanol, therefore, the water preferably varies in an amount of from about 0.1 to about 9.9% by wt. of methanol as the caustic is permitted to vary in an amount of from about 9.9 to about 0.1% by wt. of methanol, with the combined maximum amount permitted being about 10% by weight of the methanol. More preferably, water is present in an amount from about 0.1% to about 8% by wt. of the methanol, most preferably from about 0.1% to about 6% by wt. of the methanol.

The amount of methanol added to the starting material should be sufficient to cause phase formation. In addition to other factors, the amount of tocopherol present in the starting material will influence the determination of what optimum amount of methanol should be used. If, for example, the tocopherol content of the feed material is small (for example, 1 or 2% by wt. of the methanol) a smaller amount of methanol will be needed to extract a greater percentage of the desired material. If, however, a large amount of the desired tocopherol is present in the feed material (say, for example 50% by wt. of the feed) the use of a minimum amount of caustic methanol giving a two phase system would leave a larger amount of extractable, desired tocopherols which could be obtained if a larger quantity of methanol is used. In any case, the amount of methanol used must be equal to or greater than the amount of tocopherol in the feed material.

It should be kept in mind, however, that as previously indicated, other factors such as individual desires and needs also influence the determined amount of methanol used. Individually flexible factors, such as the intended use of the product, type of feed material and type of apparatus used also influences the acceptable ratio of the amount of methanol used relative to the amount of tocopherol present in the feed material. The range of this ratio is therefore very broad. The amount of methanol used relative to the amount of tocopherol present in the feed material acceptably must be greater than about 1:1, and preferably greater than 2:1. The maximum amount of methanol permitted is not critically limited, and is rather a question of practicality. Thus the ratio of methanol to tocopherol can be as high as 25:1. A preferred range of the ratio of the amount of methanol used relative to the amount of tocopherol in the feed material is from about 1:1 to about 10:1. It can be noted that where the tocopherol is largely or only alpha-tocopherol the amount of methanol should be increased. In such a case the preferred range of the ratio of methanol to alphatocopherol in the feed is at least 3 or 4:1.

After the formation of the polar, tocopherol-enriched caustic methanol phase and the non-polar organic impurities phase, the two phases are separated by any convenient method, and the polar, tocopherol-enriched caustic methanol phase should be neutralized before tocopherol recovery. Neutralization can be accomplished with anything more acidic than the tocopherols. Thus, in this description the term "neutralizing acid" includes salts, minerals acids, and amines which are more acidic than tocopherols, and thus are capable of neutralization. Acceptably, such a neutralizing acid can be used which has a $pK_a$ less than 10, or which will form a precipitate. Any acidic resin, mineral, salt, or organic acid is acceptable. Preferably, the $pK_a$ should be 8 or less. Representative, but non-exhaustive examples of preferred acids are: phosphoric, phosphonic, hydrochloric, hydrobromic, hydroiodic, hydrofluoric, nitric, sulfuric, sulfonic, sulfurous, and acetic and amine salt thereof. Most preferred is acetic acid due to the solubility of the acetate salt.

The use of an acidic resin in neutralization is a preferred embodiment of the instant invention. After such a neutralization step is completed, recovery of the tocopherol from the substantially neutral methanol is facilitated. More specifically, after the methanol is substantially neutralized, the tocopherol can be recoverd by extraction or phase formation with the presence of a sufficient amount of water (as previously indicated); or, the material more volatile than the tocopherol can be distilled and the resin removed to complete product recovery.

Even when water, or an aliphatic hydrocarbon solvent is used, whether or not phase formation occurs, all of the previously indicated mechanisms of phase formation, filtration of precipitates, and distillation can be used to separate the desired tocopherol product from the other material. These methods can be used in any effective, convenient combination or sequence.

Neutralization results in the separation of the tocopherol from the methanol phase when a sufficient amount of water is used with the neutralizing acid. As a preferred embodiment this will eliminate the necessity of adding water after neutralization and causes the formation of tocopherol as a separate phase during neutralization. When the tocopherol phase forms, it can be separated from the aqueous methanol phase which then contains the insoluble salt. If the salt formed by neutralization is partially or even totally insoluble, the precipitate formed must also be separated from the tocopherol. In this case, preferably filtration is used in addition to liquid phase separation or distillation, in order to obtain the tocopherol product.

If neutralization is accomplished without water then water can be added to cause the tocopherol to separate from the neutralized methanol and form a separate organic tocopherol phase. This organic phase, without the use of a non-polar organic solvent, will be in excess of 60% by wt. tocopherol. If the feed material had a limited amount of alpha-tocopherol (less than about 25% by wt. of the tocopherol content) then a product in excess of 75% by wt. tocopherol can be achieved without using an aliphatic hydrocarbon solvent.

In any embodiment of this process when using an aliphatic hydrocarbon solvent, any aliphatic (straight or branched chain) hydrocarbon that is at least semi-immiscible in methanol is acceptable. Suitably any aliphatic hydrocarbon having from about 5 to about 15 carbon atoms can be used. Representative of these are pentane, hexane, heptane, octane, nonane and decane. Furthermore, any blend or mixture of aliphatic hydrocarbons, or even a kerosene blend which will form an immiscible phase with the caustic methanol is suitable.

Another preferred method involves the addition of an aliphatic hydrocarbon solvent to the separated tocopherol-enriched methanol phase in order to facilitate tocopherol separation. This can be used whether or not an aliphatic hydrocarbon solvent was used in the initial extraction. The addition of this aliphatic hydrocarbon solvent can be before, during or after the addition of the aqueous or non-aqueous neutralizing acid or the water. The aliphatic hydrocarbon solvent will form a separate phase. If tocopherol separation occurs, either in neutralization, a sufficient amount of water being present, or by the addition of a sufficient amount of water after neutralization, the tocopherol, along with any aliphatic hydrocarbon which was solvated with the caustic methanol during the first step, will form a second phase joining the aliphatic hydrocarbon solvent added after separation of the tocopherol-enriched caustic methanol. The tocopherol-enriched aliphatic hydrocarbon phase formed is then separated and can be distilled to isolate the tocopherol or can be subjected to further tocopherol processing such as methylation.

Alternatively, it is also possible when using an aliphatic hydrocarbon solvent, to take advantage of the decrease in solubility of the tocopherol in the methanol, after it is neutralized. In this embodiment, water need not be added to the methanol to obtain the phase separation. Instead the tocopherol is extracted into the contacting aliphatic hydrocarbon phase, and this phase is then separated to complete recovery. For maximum tocopherol extraction, however, water should be added to cause tocopherol phase separation. As was previously indicated, the recovered tocopherol can be further processed in the aliphatic hydrocarbon solvent, used as an anti-oxidizing composition, or further isolated by distillation.

Preferably any tocopherol product recovered at the end of this process with or without the presence of an aliphatic hydrocarbon solvent is subjected to one or more washes with water to remove any residual salt formed by the caustic and neutralizing acid.

The amount of aliphatic hydrocarbon solvent preferably used with the process of the instant invention either to separate the organic feed material and its impurities, or later to collect the tocopoherol from the aqueous methanol should be at least in that minimum that is sufficient to provide a second phase. This minimum amount needed will be influenced by the amount of material solvating with it in that phase. More aliphatic hydrocarbon solvent should be used when there is more material to be separated with it. To a great extent, however, the amount of aliphatic hydrocarbon solvent used will depend on individual needs in addition to the amount of material there is to separate. The maximum amount of aliphatic hydrocarbon solvent is flexible, and is a question of practicality. The amount of aliphatic hydrocarbon solvent used for either phase separation is therefore very broad. Acceptably, the range can be from about 0.2 parts aliphatic solvent per total amount of material to about 20 parts aliphatic solvent per total amount of material that the solvent is added to.

The temperatures and pressures used in conjunction with the extraction steps of the instant process should be sufficient to maintain the materials as liquid. Within this limitation any particular temperature or pressure required by any particular extraction apparatus or phase separation system is acceptable as long as no decomposition or oxidation of the tocopherol occurs. Naturally, where the methanol or aliphatic hydrocarbon solvent is being separated from the tocopherol by distillation or evaporation, the temperature and pressure required by the particular method of distillation should be used. Likewise a variety of distillation techniques and apparatus are available and may be selected for use with the process of the instant invention. It is sufficient that no decomposition of the tocopherol occurs when the methanol is being removed by the particular distillation or evaporation technique selected.

When the tocopherol is in contact with the caustic the use of an inert atmosphere is preferred since oxidation of tocopherol can occur. Such an inert atmosphere should be maintained over the tocopherol-enriched methanol phase as long as unneutralized caustic is present. Thereby, oxidation of the tocopherol is drastically reduced if not eliminated. Any gas or mixture of gases nonreactive to caustic is suitable. Representative, but non-exhaustive examples of gases which can provide such an inert atmosphere are nitrogen, argon, helium, methane and ethane. Another way to avoid or minimize oxidation of tocopherol when it is in contact with caustic, however, is to minimize the length of time of this contact.

When using the process of the instant invention any technique and apparatus used and suited to extraction processes can be employed. It is possible and permissible for example to backwash the tocopherol-enriched caustic methanol phase with a portion of an aliphatic hydrocarbon solvent in order to collect any unwanted hydrocarbon impurities. It is also acceptable, when collecting the tocopherol from the neutral methanol phase, to wash the neutralized methanol material with several portions of an aliphatic hydrocarbon solvent such as hexane in order to collect the maximum amount of tocopherol. Preferably the neutralized methanol is washed at least twice with the solvent. The solvent can then be distilled and the tocopherol collected.

It can be readily appreciated that the tocopherol-containing phase, from which the tocopherol is being removed, can be re-washed by repeated, successive contacts by the extracting phase material into which the tocopherol is going. Additionally, tocopherol removal from the neutralized aqueous methanol can be maximized by repeated contacts with an aliphatic hydrocarbon solvent. Continuous extraction systems can be used to obtain these repeat contacts or their effects, thereby achieving maximum tocopherol removal.

The process of the instant invention will be more fully understood from the examples which follow. These examples are intended to clarify and demonstrate the instant invention and not to limit it. All parts and percentages are by wt. unless otherwise specified.

EXAMPLE I

A 100 gram (g) portion of a tocopherol-concentrated soybean oil as the organic feed material was used which included the following materials:
21.2% co-boiling hydrocarbons,
6.7% sterols, and
60.6% tocopherol homologues of the following composition: 17.1% delta-; 38.3% beta-gamma-; and 5.2% alpha-.

This feed material was dissolved in 200 g of hexane. The resulting mixture was then contacted with 300 g of methanol, and 15 g of sodium hydroxide. Two phases formed which were: (1) tocopherol-enriched caustic methanol phase; and (2) hexane phase containing the separated organic impurities of the original feed material.

These two phases were separated and the tocopherol-enriched caustic methanol phase was contacted three times with 100 g portions of hexane to optimize the removal of organic impurities. These hexane layers were combined and were then contacted three times with an additional portion of 100 g methanol with 5 g of sodium hydroxide to prevent loss of tocopherol. These caustic methanol layers were then combined and all of the hexane phases which had been collected were discarded. The resulting tocopherol-enriched caustic methanol was then neutralized with glacial acetic acid (nonaqueous). This was accomplished by the addition of the glacial acetic acid until a pH of 6 was obtained.

No separation occurred at this point. 100 g of water was then added and phase separation occurred resulting in two phases.

The separation occurring when the water was added resulted in a tocopherol-enriched hexane containing phase. This hexane-tocopherol phase was separated and the neutralized methanol phase was washed with another 100 g portion of hexane. These two hexane phases were combined and the hexane was removed under a vacuum leaving a product which was: 81.6% total tocopherol; 6.6% total sterols; 2% coboiling hydrocarbons. The tocopherols in the product had the following composition: 24.1% (by wt.) delta-; 51.8% (by wt.) beta-gamma-; and 5.7% (by wt.) alpha-.

EXAMPLE II

The four experiments of this example were conducted in the following manner. The amount of 75 g methanol was combined with the indicated amount of sodium hydroxide for each separate experiment. In each case the feed material used was tocopherol concentrate from soybean oil. The weight percent of the low-boiling impurities and the tocopherol homologues in this feed material is indicated. In each of the four cases, 25 g of the feed material was combined with 50 g of hexane, and then contacted with the caustic methanol solution. Two phases formed, and were separated. The caustic methanol tocopherol-enriched material, which was the material of one phase, was neutralized with acetic acid, and 50 mililiters (ml) of water was added to it. This solution was then contacted with 100 ml of hexane to extract the tocopherol. The tocopherol-enriched hexane from this extraction was then washed with water and the hexane was then removed from the tocopherol using a vacuum distillation. Also present in the raffinate is the hexane, which was initially added to the feed material before the first extraction. This hexane was removed by vacuum distillation and the content of the raffinate was analyzed. The raffinate of the first extraction containing the remaining feed material had been contacted only once with caustic methanol. In all four cases, however, the feed material left in the raffinate was largely low-boiling impurities, and only small percentages of each tocopherol homologue remained. The results of the analysis are specifically indicated in the following data.

TABLE

| | | | Example II | | | |
|---|---|---|---|---|---|---|
| | | | content in wt. % of material analyzed | | | |
| Example No. | g of NaOH | material analyzed | $\delta$ tocopherol | $\beta$-$\gamma$ tocopherol | $\alpha$ tocopherol | low boiling impurities |
| 1 | 7.5 | Extracted Material | 20.9 | 42.7 | 5.4 | 19.0 |
| | | Feed Material Raffinate | 7.8 | 16.6 | 2.3 | 70.9 |
| 2 | 3.75 | Extracted | 23.8 | 49.3 | 5.7 | 11.26 |

TABLE-continued

Example II

| | | Material | | | | |
|---|---|---|---|---|---|---|
| | | Feed Material | 3.2 | 7.0 | 2.0 | 87.6 |
| | | Raffinate | | | | |
| 3 | 1.88 | Extracted | 22.4 | 46.2 | 5.4 | 17.5 |
| | | Material | | | | |
| | | Feed Material | 2.9 | 8.1 | 2.3 | 84.7 |
| | | Raffinate | | | | |
| 4 | .38 | Extracted | 17.6 | 37.3 | 4.7 | 34.5 |
| | | Material | | | | |
| | | Feed Material | 7.4 | 19.3 | 3.1 | 65.7 |
| | | Left in Raffinate | | | | |

| Feed Material Used: | tocopherol wt. % δ | tocopherol wt. % β-γ | tocopherol wt. % α | low boiling impurities |
|---|---|---|---|---|
| | 17.2 | 36.6 | 4.6 | 36.0 |

To appreciate the extent of purification of the tocopherol removed from the feed material, the content of the raffinate in weight percent is compared to the content of the extracted phase material. The original feed material, without any solvent, was 36.0 weight percent in low-boiling impurities. The feed material raffinate, which was analyzed after the hexane was removed by vacuum distillation, indicates that the low-boiling impurities comprised most of the raffinate. Thus, the weight percent of the low-boiling impurities in this material increased while conversely the tocopherol in the feed material raffinate was lower. It is also noteworthy that where a larger amount of sodium hydroxide was used, the instant invention displayed more success in the isolation of tocopherol, and in leaving behind the low-boiling impurities in the feed material.

EXAMPLE III

In this example, seven experiments were completed in which a specific amount of tocopherol-concentrated soybean oil, solvated with a specific amount of aliphatic hydrocarbon solvent, was contacted once with caustic methanol. The same purification and recovery process was used in each of the seven experiments under this example. The base and the aliphatic hydrocarbon solvent used was varied; the caustic being either KOH or NaOH, and the aliphatic hydrocarbon being either hexane or octane. This enables a comparison of the performance of NaOH vs. KOH, and octane vs. hexane. The amount (in wt. %) of the low-boiling impurities and of each tocopherol homologue was analyzed twice, both in the original feed material left in the raffinate after one extraction with the caustic methanol, and in the recovered product solvated in the hexane or octane used to recover the tocopherol product. This data is listed in the table.

The following procedure was used for each of the seven experiments. 50 g of hexane or n-octane were mixed with 25 g of tocopherol concentrated soybean oil(the feed material) which included the amounts of the low-boiling impurities and the tocopherol homologues indicated below the table. This mixture was contacted with a solution of 75 g methanol containing either 3.75 g of NaOH or 6.18 g of KOH (containing 15% by weight water).

Each extraction was agitated for five minutes and permitted to settle; the phases were then separated and the caustic methanol was neutralized with acetic acid. The tocopherol product was recovered by extracting it from the neutralized material with 50 g of hexane. As previously indicated, the data is listed in the table below. For each experiment two separate analyses were taken, both of the recovered product and of the raffinate feed material left after the initial caustic methanol extraction. The data reflects amounts in % by weight of the total, which are the average of the two analysis results. Comparison of this data with the tocopherol homologue and low-boiling impurities content in the original feed material shows that the tocopherol was purified and concentrated.

TABLE

Example III

| Example No. | Kind & Amount of Base | Aliphatic Hydrocarbon (50 g) | Recovered Product and Remaining Feed Material in Raffinate | (wt. %) of: Tocopherol δ | β-γ | α | Low Boiling Impurities |
|---|---|---|---|---|---|---|---|
| 1 | 3.75 g NaOH | Hexane | Recovered Product (Analysis) | 23.5 | 50.05 | 5.9 | 14.3 |
| | | | Feed Material in Raffinate | 3.1 | 7.8 | 2.0 | 89.95 |
| 2 | 3.75 g NaOH | Hexane | Recovered Product | 23.3 | 49.6 | 5.8 | 13.6 |
| | | | Feed Material in Raffinate | 3.0 | 7.4 | 1.95 | 87.75 |
| 3 | 3.75 g NaOH | N—Octane | Recovered Product | 25.7 | 53.75 | 6.05 | 7.1 |
| | | | Feed Material In Raffinate | 3.35 | 9.4 | 2.6 | 85.5 |
| 4 | 6.18 g KOH | Hexane | Recovered Product | 24.4 | 52.2 | 6.0 | 13.0 |
| | | | Feed Material In Raffinate | 4.05 | 9.4 | 2.25 | 86.3 |
| 5 | 6.18 g KOH | Hexane | Recovered Product | 24.25 | 51.7 | 5.75 | 13.1 |

TABLE-continued

| Example No. | Kind & of Amount Base | Aliphatic Hydrocarbon (50 g) | Example III Recovered Product and Remaining Feed Material in Raffinate | (wt. %) of: | | | |
|---|---|---|---|---|---|---|---|
| | | | | Tocopherol | | | Low Boiling Impurities |
| | | | | δ | β-γ | α | |
| 6 | 6.18 g KOH | N—Octane | Feed Material In Raffinate | 3.8 | 9.35 | 2.2 | 86.6 |
| | | | Recovered Product | 26.95 | 56.2 | 6.1 | 7.6 |
| | | | Feed Material In Raffinate | 4.4 | 11.5 | 2.85 | 81.05 |
| 7 | 6.18 g KOH | N—Octane | Recovered Product | 25.75 | 54.3 | 6.05 | 7.45 |
| | | | Feed Material In Raffinate | 4.6 | 11.35 | 2.8 | 80.4 |

The Percentage by Weight Content of the Feed Material:
Tocopherols: 16.7–16.9% δ; 36.5–36.9% β-γ; 4.6–4.7% α
Low boiling Impurities: 36.3–36.8%

As indicated, the feed material was approximately 36.5% by weight low-boiling impurities, yet comparatively in all seven experiments, the wt. % of the low-boiling impurities which remained in the raffinate feed material was much larger. In fact, the low-boiling impurities remaining in the feed material in the raffinate in these experiments was a minimum of 80.2% weight. Simultaneously, the tocopherol content of the feed material left in the raffinate substantially decreased after just one extraction. Moreover, each tocopherol homologue is present in a substantially larger weight percent in the recovered product material than it did in the feed material. This example thus shows that tocopherol was purified and concentrated using the process of the instant invention.

What is claimed is:

1. A process for obtaining tocopherol from organic material containing such, comprising:
   (a) contacting the organic material containing tocopherol with a sufficient amount of caustic methanol whereby two phases are formed, one being a tocopherol-enriched caustic methanol solution, and the other being an organic phase,
   (b) separating the two phases,
   (c) contacting the tocopherol-enriched caustic methanol with a neutralizing acid whereby the methanol becomes a substantially neutralized solution, and
   (d) recovering the tocopherol from the substantially neutralized methanol solution.

2. A process as described in claim 1 wherein the organic material containing the tocopherol is contacted with a sufficient amount of both caustic methanol and an aliphatic hydrocarbon solvent to form the two phases each having some aliphatic hydrocarbon; and the phases are then separated, the tocopherol-enriched caustic methanol is neutralized, and the tocopherol is recovered.

3. A process as described in claim 2 wherein the organic material is contacted with caustic methanol also containing water in an amount of from about 0.1 to about 9.9% by weight of the methanol while the caustic is in an amount of from about 0.1 to about 9.9% by weight of the methanol, provided that the combined maximum of the water and caustic is not greater than about 10% by weight of the methanol.

4. A process as described in claim 3 wherein water is added to the tocopherol-enriched caustic methanol during or after neutralization step (c) in a sufficient amount to cause phase separation whereby the phases formed are: (1) a substantially neutral salt-containing methanol phase, and (2) a tocopherol phase also containing some of the aliphatic hydrocarbon solvent from step (a); and the tocopherol is recovered by separating the tocopherol phase.

5. A process as described in claim 4 wherein an aliphatic hydrocarbon solvent is added to the tocopherol-enriched aqueous methanol during or after neutralization in a sufficient amount with the water to form an aqueous methanol phase, and a tocopherol-enriched aliphatic hydrocarbon phase; the tocopherol-enriched aliphatic hydrocarbon phase is then separated, and the tocopherol is recovered.

6. A process as described in claim 5 wherein the aliphatic hydrocarbon solvent is distilled away from the tocopherol after separation.

7. A process as described in claim 4 wherein acetic acid is used for neutralization.

8. A process as described in claim 2 wherein the salt formed in neutralization forms a precipitate, and the tocopherol enriched, substantially neutralized methanol material is distilled to recover the tocopherol.

9. A process as described in claim 8 wherein the acid is a mineral acid, and the salt precipitated is removed by filtration.

10. A process as described in claim 3 wherein the tocopherol recovered by contacting the tocopherol-enriched, substantially neutralized, methanol with an aliphatic hydrocarbon solvent whereby the tocopherol is extracted into the aliphatic hydrocarbon solvent, and then separating the tocopherol containing aliphatic hydrocarbon solvent.

11. A process as described in claim 3 wherein the acid is an acidic ion exchange resin which exchanges hydrogen ions for basic ions present in the tocopherol-enriched caustic methanol.

12. A process as described in claim 11 wherein the tocopherol-enriched methanol is separated from the resin after substantial neutralization has occurred, and the tocopherol is then separated from it by distillation.

13. A process as described in claim 11 wherein the tocopherol-enriched methanol is separated from the resin after substantial neutralization has occurred; and thereafter adding a sufficient amount of water to form two phases, one being aqueous methanol, the other being substantially tocopherol with some aliphatic hydrocarbon; and separating the tocopherol and aliphatic hydrocarbon phase.

14. A process as described in claim 3 wherein the tocopherol is extracted from the methanol after substantial neutralization has occurred by contacting the tocopherol-enriched methanol with an aliphatic hydrocarbon solvent, thereby extracting the tocopherol from the methanol, and then separating the tocopherol-enriched aliphatic hydrocarbon.

* * * * *